(12) United States Patent
Gustus et al.

(10) Patent No.: US 8,401,667 B2
(45) Date of Patent: Mar. 19, 2013

(54) SELECTIVE ACCUMULATION OF ENERGY WITH OR WITHOUT KNOWLEDGE OF TISSUE TOPOGRAPHY

(75) Inventors: Rolfe Tyson Gustus, San Diego, CA (US); Linas Kunstmanas, Valley Center, CA (US); Arthur G. Blanck, Ramona, CA (US)

(73) Assignee: Vessix Vascular, Inc., Laguna Hills, CA (US)

( * ) Notice: Subject to any disclaimer, the term of this patent is extended or adjusted under 35 U.S.C. 154(b) by 285 days.

(21) Appl. No.: 12/617,519

(22) Filed: Nov. 12, 2009

(65) Prior Publication Data

US 2010/0125268 A1 May 20, 2010

Related U.S. Application Data

(60) Provisional application No. 61/115,344, filed on Nov. 17, 2008.

(51) Int. Cl.
*A61F 7/12* (2006.01)
(52) U.S. Cl. .............................. 607/99; 607/96; 607/98
(58) Field of Classification Search ................... 607/96, 607/98, 99; 606/7, 32, 41
See application file for complete search history.

(56) References Cited

U.S. PATENT DOCUMENTS

| | | |
|---|---|---|
| 1,167,014 A | 1/1914 | O'Brien |
| 2,505,358 A | 4/1950 | Gusberg et al. |
| 2,701,559 A | 2/1955 | Cooper |
| 3,108,593 A | 10/1963 | Glassman |
| 3,108,594 A | 10/1963 | Glassman |
| 3,540,431 A | 11/1970 | Mobin-Uddin |
| 3,952,747 A | 4/1976 | Kimmell, Jr. |
| 3,996,938 A | 12/1976 | Clark, III |
| 4,046,150 A | 9/1977 | Schwartz et al. |
| 4,290,427 A | 9/1981 | Chin |
| 4,587,975 A | 5/1986 | Salo et al. |
| 4,682,596 A | 7/1987 | Bales et al. |
| 4,709,698 A | 12/1987 | Johnston et al. |
| 4,770,653 A | 9/1988 | Shturman |
| 4,784,132 A | 11/1988 | Fox et al. |

(Continued)

FOREIGN PATENT DOCUMENTS

| | | |
|---|---|---|
| CA | 2384866 A1 | 5/2001 |
| CN | 101583323 A | 11/2009 |

(Continued)

OTHER PUBLICATIONS

International Search Report and Written Opinion of PCT Application No. PCT/US2009/064027, mailed on Jan. 19, 2010, 9 pages total.

(Continued)

*Primary Examiner* — Roy Gibson
(74) *Attorney, Agent, or Firm* — Kilpatrick Townsend & Stockton LLP

(57) ABSTRACT

Methods and systems for heating a body tissue region adjacent a body lumen using selective accumulation of energy without knowledge of tissue topography. Methods include positioning an energy delivery portion of a catheter within the lumen adjacent the body tissue region, determining a pulse characteristic in response to a thermal property of a first tissue type and applying pulsed energy with the characteristic to treat a second tissue type within the region by drawing heat from the first tissue at a rate that inhibits thermal damage to the first tissue while building-up heat in the second tissue. Systems include a catheter body having an energy delivery portion processor configured to control a pulse characteristic of pulsed energy to therapeutically treat the second tissue by drawing heat from the first tissue at a rate that inhibits thermal damage to the first tissue while building-up heat in the second tissue.

40 Claims, 4 Drawing Sheets

U.S. PATENT DOCUMENTS

| | | |
|---|---|---|
| 4,785,806 A | 11/1988 | Deckelbaum |
| 4,799,479 A | 1/1989 | Spears |
| 4,862,886 A | 9/1989 | Clarke et al. |
| 4,955,377 A | 9/1990 | Lenno et al. |
| 4,976,711 A | 12/1990 | Parins et al. |
| 5,053,033 A | 10/1991 | Clarke |
| 5,071,424 A | 12/1991 | Reger |
| 5,074,871 A | 12/1991 | Groshong |
| 5,098,429 A | 3/1992 | Sterzer |
| 5,098,431 A | 3/1992 | Rydell |
| 5,102,402 A | 4/1992 | Dror et al. |
| RE33,925 E | 5/1992 | Bales et al. |
| 5,109,859 A | 5/1992 | Jenkins |
| 5,125,928 A | 6/1992 | Parins et al. |
| 5,129,396 A | 7/1992 | Rosen et al. |
| 5,156,610 A | 10/1992 | Reger |
| 5,158,564 A | 10/1992 | Schnepp-Pesch et al. |
| 5,178,620 A | 1/1993 | Eggers et al. |
| 5,178,625 A | 1/1993 | Groshong |
| 5,190,540 A | 3/1993 | Lee |
| 5,211,651 A | 5/1993 | Reger et al. |
| 5,263,493 A | 11/1993 | Avitall |
| 5,277,201 A | 1/1994 | Stern |
| 5,282,484 A | 2/1994 | Reger |
| 5,286,254 A | 2/1994 | Shapland et al. |
| 5,304,121 A | 4/1994 | Sahatjian |
| 5,304,171 A | 4/1994 | Gregory et al. |
| 5,304,173 A | 4/1994 | Kittrell et al. |
| 5,306,250 A | 4/1994 | March et al. |
| 5,322,064 A | 6/1994 | Lundquist |
| 5,330,518 A | 7/1994 | Neilson et al. |
| 5,380,319 A | 1/1995 | Saito et al. |
| 5,383,917 A | 1/1995 | Desai et al. |
| 5,409,000 A | 4/1995 | Imran |
| 5,419,767 A | 5/1995 | Eggers et al. |
| 5,453,091 A | 9/1995 | Taylor et al. |
| 5,454,809 A | 10/1995 | Janssen |
| 5,474,530 A | 12/1995 | Passafaro et al. |
| 5,496,311 A | 3/1996 | Abele et al. |
| 5,496,312 A | 3/1996 | Klicek |
| 5,498,261 A | 3/1996 | Strul |
| 5,540,681 A | 7/1996 | Strul et al. |
| 5,545,161 A | 8/1996 | Imran |
| 5,562,100 A | 10/1996 | Kittrell et al. |
| 5,571,122 A | 11/1996 | Kelly et al. |
| 5,571,151 A | 11/1996 | Gregory |
| 5,573,531 A | 11/1996 | Gregory |
| 5,573,533 A | 11/1996 | Strul |
| 5,588,962 A | 12/1996 | Nicholas et al. |
| 5,599,346 A | 2/1997 | Edwards et al. |
| 5,609,606 A | 3/1997 | O'Boyle |
| 5,626,576 A | 5/1997 | Janssen |
| 5,643,297 A | 7/1997 | Nordgren et al. |
| 5,647,847 A | 7/1997 | Lafontaine et al. |
| 5,649,923 A | 7/1997 | Gregory et al. |
| 5,662,671 A | 9/1997 | Barbut et al. |
| 5,665,062 A | 9/1997 | Houser |
| 5,665,098 A | 9/1997 | Kelly et al. |
| 5,681,282 A | 10/1997 | Eggers |
| 5,693,029 A | 12/1997 | Leonhardt |
| 5,693,043 A | 12/1997 | Kittrell et al. |
| 5,697,369 A | 12/1997 | Long, Jr. et al. |
| 5,697,909 A | 12/1997 | Eggers et al. |
| 5,713,942 A | 2/1998 | Stern et al. |
| 5,749,914 A | 5/1998 | Janssen |
| 5,755,753 A | 5/1998 | Knowlton |
| 5,775,338 A | 7/1998 | Hastings |
| 5,776,174 A | 7/1998 | Van Tassel |
| 5,792,105 A | 8/1998 | Lin et al. |
| 5,807,306 A | 9/1998 | Shapland et al. |
| 5,817,092 A | 10/1998 | Behl |
| 5,817,144 A | 10/1998 | Gregory |
| 5,848,969 A | 12/1998 | Panescu et al. |
| 5,860,974 A | 1/1999 | Abele |
| 5,865,801 A | 2/1999 | Houser |
| 5,869,127 A | 2/1999 | Zhong |
| 5,871,524 A | 2/1999 | Knowlton |
| 5,876,369 A | 3/1999 | Houser |
| 5,876,374 A | 3/1999 | Alba et al. |
| 5,876,397 A | 3/1999 | Edelman et al. |
| 5,904,651 A | 5/1999 | Swanson et al. |
| 5,906,636 A | 5/1999 | Casscells, III et al. |
| 5,919,219 A | 7/1999 | Knowlton |
| 5,934,284 A | 8/1999 | Plaia et al. |
| 5,948,011 A | 9/1999 | Knowlton |
| 5,954,717 A | 9/1999 | Behl et al. |
| 5,999,678 A | 12/1999 | Murphy-Chutorian et al. |
| 6,010,522 A | 1/2000 | Barbut et al. |
| 6,032,675 A | 3/2000 | Rubinsky |
| 6,033,398 A | 3/2000 | Farley et al. |
| 6,036,689 A | 3/2000 | Tu et al. |
| 6,041,260 A | 3/2000 | Stern et al. |
| 6,050,994 A | 4/2000 | Sherman |
| 6,056,744 A | 5/2000 | Edwards |
| 6,056,746 A | 5/2000 | Goble et al. |
| 6,081,749 A | 6/2000 | Ingle et al. |
| 6,083,159 A | 7/2000 | Driscoll et al. |
| 6,091,995 A | 7/2000 | Ingle et al. |
| 6,117,128 A | 9/2000 | Gregory |
| 6,120,516 A | 9/2000 | Selmon et al. |
| 6,123,702 A | 9/2000 | Swanson et al. |
| 6,123,718 A | 9/2000 | Tu et al. |
| 6,129,725 A | 10/2000 | Tu et al. |
| 6,142,991 A | 11/2000 | Schatzberger |
| 6,152,899 A | 11/2000 | Farley et al. |
| 6,156,046 A | 12/2000 | Passafaro et al. |
| 6,161,048 A | 12/2000 | Sluijter et al. |
| 6,165,187 A | 12/2000 | Reger |
| 6,183,468 B1 | 2/2001 | Swanson et al. |
| 6,190,379 B1 | 2/2001 | Heuser et al. |
| 6,191,862 B1 | 2/2001 | Swanson et al. |
| 6,197,021 B1 | 3/2001 | Panescu et al. |
| 6,200,266 B1 | 3/2001 | Shokrollahi et al. |
| 6,203,561 B1 | 3/2001 | Ramee et al. |
| 6,211,247 B1 | 4/2001 | Goodman |
| 6,216,704 B1 | 4/2001 | Ingle et al. |
| 6,219,577 B1 | 4/2001 | Brown, III et al. |
| 6,228,076 B1 | 5/2001 | Winston et al. |
| 6,231,516 B1 | 5/2001 | Keilman et al. |
| 6,241,753 B1 | 6/2001 | Knowlton |
| 6,258,087 B1 | 7/2001 | Edwards et al. |
| 6,287,323 B1 | 9/2001 | Hammerslag |
| 6,293,942 B1 | 9/2001 | Goble et al. |
| 6,299,379 B1 | 10/2001 | Lewis |
| 6,299,623 B1 | 10/2001 | Wulfman |
| 6,309,379 B1 | 10/2001 | Willard et al. |
| 6,309,399 B1 | 10/2001 | Barbut et al. |
| 6,311,090 B1 | 10/2001 | Knowlton |
| 6,319,242 B1 | 11/2001 | Patterson et al. |
| 6,319,251 B1 | 11/2001 | Tu et al. |
| 6,322,559 B1 | 11/2001 | Daulton et al. |
| 6,325,799 B1 | 12/2001 | Goble |
| 6,328,699 B1 | 12/2001 | Eigler et al. |
| 6,350,276 B1 | 2/2002 | Knowlton |
| 6,353,751 B1 | 3/2002 | Swanson et al. |
| 6,364,840 B1 | 4/2002 | Crowley |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,389,311 B1 | 5/2002 | Whayne et al. |
| 6,389,314 B2 | 5/2002 | Feiring |
| 6,391,024 B1 | 5/2002 | Sun et al. |
| 6,394,956 B1 | 5/2002 | Chandrasekaran et al. |
| 6,405,090 B1 | 6/2002 | Knowlton |
| 6,409,723 B1 | 6/2002 | Edwards |
| 6,413,255 B1 | 7/2002 | Stern |
| 6,421,559 B1 | 7/2002 | Pearlman |
| 6,423,057 B1 | 7/2002 | He et al. |
| 6,425,912 B1 | 7/2002 | Knowlton |
| 6,430,446 B1 | 8/2002 | Knowlton |
| 6,438,424 B1 | 8/2002 | Knowlton |
| 6,445,939 B1 | 9/2002 | Swanson et al. |
| 6,453,202 B1 | 9/2002 | Knowlton |
| 6,454,775 B1 | 9/2002 | Demarais et al. |
| 6,458,098 B1 | 10/2002 | Kanesaka |

| Patent | Date | Inventor |
|---|---|---|
| 6,461,378 B1 | 10/2002 | Knowlton |
| 6,470,216 B1 | 10/2002 | Knowlton |
| 6,477,426 B1 | 11/2002 | Fenn et al. |
| 6,482,202 B1 | 11/2002 | Goble et al. |
| 6,485,489 B2 | 11/2002 | Teirstein et al. |
| 6,488,679 B1 | 12/2002 | Swanson et al. |
| 6,497,711 B1 | 12/2002 | Plaia et al. |
| 6,508,765 B2 | 1/2003 | Suorsa et al. |
| 6,511,496 B1 | 1/2003 | Huter et al. |
| 6,522,926 B1 | 2/2003 | Kieval et al. |
| 6,540,761 B1 | 4/2003 | Houser |
| 6,546,272 B1 | 4/2003 | MacKinnon et al. |
| 6,552,796 B2 | 4/2003 | Magnin et al. |
| 6,558,381 B2 | 5/2003 | Ingle et al. |
| 6,558,382 B2 | 5/2003 | Jahns et al. |
| 6,569,109 B2 | 5/2003 | Sakurai et al. |
| 6,569,177 B1 | 5/2003 | Dillard et al. |
| 6,570,659 B2 | 5/2003 | Schmitt |
| 6,582,423 B1 | 6/2003 | Thapliyal et al. |
| 6,589,238 B2 | 7/2003 | Edwards et al. |
| 6,592,526 B1 | 7/2003 | Lenker |
| 6,605,061 B2 | 8/2003 | Vantassel et al. |
| 6,623,453 B1 | 9/2003 | Guibert et al. |
| 6,632,193 B1 | 10/2003 | Davison et al. |
| 6,632,196 B1 | 10/2003 | Houser |
| 6,673,066 B2 | 1/2004 | Werneth |
| 6,673,290 B1 | 1/2004 | Whayne et al. |
| 6,690,181 B1 | 2/2004 | Dowdeswell et al. |
| 6,692,490 B1 | 2/2004 | Edwards |
| 6,695,830 B2 | 2/2004 | Vigil et al. |
| 6,706,011 B1 | 3/2004 | Murphy-Chutorian et al. |
| 6,706,037 B2 | 3/2004 | Zvuloni et al. |
| 6,714,822 B2 | 3/2004 | King et al. |
| 6,720,350 B2 | 4/2004 | Kunz et al. |
| 6,723,064 B2 | 4/2004 | Babaev |
| 6,736,811 B2 | 5/2004 | Panescu et al. |
| 6,748,953 B2 | 6/2004 | Sherry et al. |
| 6,760,616 B2 | 7/2004 | Hoey et al. |
| 6,769,433 B2 | 8/2004 | Zikorus et al. |
| 6,771,996 B2 | 8/2004 | Bowe et al. |
| 6,786,904 B2 | 9/2004 | Doscher et al. |
| 6,788,977 B2 | 9/2004 | Fenn et al. |
| 6,807,444 B2 | 10/2004 | Tu et al. |
| 6,829,497 B2 | 12/2004 | Mogul |
| 6,845,267 B2 | 1/2005 | Harrison et al. |
| 6,849,073 B2 | 2/2005 | Hoey et al. |
| 6,853,425 B2 | 2/2005 | Kim et al. |
| 6,926,716 B2 | 8/2005 | Baker et al. |
| 6,932,776 B2 | 8/2005 | Carr |
| 6,936,047 B2 | 8/2005 | Nasab et al. |
| 6,953,425 B2 | 10/2005 | Brister |
| 6,955,174 B2 | 10/2005 | Joye |
| 6,958,075 B2 | 10/2005 | Mon et al. |
| 6,962,584 B1 | 11/2005 | Stone |
| 6,964,660 B2 | 11/2005 | Maguire et al. |
| 6,972,024 B1 | 12/2005 | Kilpatrick et al. |
| 6,991,617 B2 | 1/2006 | Hektner et al. |
| 7,008,667 B2 | 3/2006 | Chudzik et al. |
| 7,011,508 B2 | 3/2006 | Lum |
| 7,066,904 B2 | 6/2006 | Rosenthal et al. |
| 7,104,987 B2 | 9/2006 | Biggs et al. |
| 7,137,980 B2 | 11/2006 | Buysse et al. |
| 7,162,303 B2 | 1/2007 | Levin et al. |
| 7,192,427 B2 | 3/2007 | Chapelon et al. |
| 7,200,445 B1 | 4/2007 | Dalbec et al. |
| 7,252,664 B2 | 8/2007 | Nasab et al. |
| 7,288,096 B2 | 10/2007 | Chin |
| 7,291,146 B2 | 11/2007 | Steinke et al. |
| 7,326,235 B2 | 2/2008 | Edwards |
| 7,407,671 B2 | 8/2008 | McBride et al. |
| 7,425,212 B1 | 9/2008 | Danek et al. |
| 7,426,409 B2 | 9/2008 | Casscells, III et al. |
| 7,497,858 B2 | 3/2009 | Chapelon et al. |
| 7,556,624 B2 | 7/2009 | Laufer et al. |
| 7,617,005 B2 | 11/2009 | Demarais et al. |
| 7,632,268 B2 | 12/2009 | Edwards et al. |
| 7,653,438 B2 | 1/2010 | Deem et al. |
| 7,691,080 B2 | 4/2010 | Seward et al. |
| 7,717,948 B2 | 5/2010 | Demarais et al. |
| 7,854,734 B2 | 12/2010 | Biggs et al. |
| 7,862,565 B2 | 1/2011 | Eder et al. |
| 7,901,400 B2 | 3/2011 | Wham et al. |
| 7,942,874 B2 | 5/2011 | Eder et al. |
| 2001/0051774 A1 | 12/2001 | Littrup et al. |
| 2002/0072686 A1 | 6/2002 | Hoey et al. |
| 2002/0077592 A1 | 6/2002 | Barry |
| 2002/0087156 A1 | 7/2002 | Maguire et al. |
| 2002/0107511 A1 | 8/2002 | Collins et al. |
| 2002/0143324 A1 | 10/2002 | Edwards |
| 2003/0004510 A1 | 1/2003 | Wham et al. |
| 2003/0028114 A1 | 2/2003 | Casscells, III et al. |
| 2003/0060857 A1 | 3/2003 | Perrson et al. |
| 2003/0060858 A1 | 3/2003 | Kieval et al. |
| 2003/0069619 A1 | 4/2003 | Fenn et al. |
| 2003/0195501 A1 | 10/2003 | Sherman et al. |
| 2003/0212394 A1 | 11/2003 | Pearson et al. |
| 2003/0220639 A1 | 11/2003 | Chapelon et al. |
| 2003/0229340 A1 | 12/2003 | Sherry et al. |
| 2003/0229384 A1 | 12/2003 | Mon |
| 2004/0000633 A1 | 1/2004 | Casper et al. |
| 2004/0062852 A1 | 4/2004 | Schroeder et al. |
| 2004/0073206 A1 | 4/2004 | Foley et al. |
| 2004/0111016 A1 | 6/2004 | Casscells, III et al. |
| 2004/0181165 A1 | 9/2004 | Hoey et al. |
| 2004/0186468 A1 | 9/2004 | Edwards |
| 2004/0220556 A1 | 11/2004 | Cooper et al. |
| 2004/0243199 A1 | 12/2004 | Mon et al. |
| 2005/0010208 A1 | 1/2005 | Winston et al. |
| 2005/0015125 A1 | 1/2005 | Mioduski et al. |
| 2005/0096647 A1 | 5/2005 | Steinke et al. |
| 2005/0203434 A1 | 9/2005 | Kassab |
| 2005/0203498 A1 | 9/2005 | Mon et al. |
| 2005/0251116 A1 | 11/2005 | Steinke et al. |
| 2005/0283195 A1 | 12/2005 | Pastore et al. |
| 2006/0085054 A1 | 4/2006 | Zikorus et al. |
| 2006/0089638 A1 | 4/2006 | Carmel et al. |
| 2006/0184060 A1 | 8/2006 | Belalcazar et al. |
| 2006/0235286 A1 | 10/2006 | Stone et al. |
| 2006/0246143 A1 | 11/2006 | Ege |
| 2007/0078498 A1 | 4/2007 | Stone et al. |
| 2007/0173805 A1 | 7/2007 | Rezai et al. |
| 2007/0173899 A1 | 7/2007 | Levin et al. |
| 2007/0197891 A1 | 8/2007 | Shachar et al. |
| 2007/0265687 A1 | 11/2007 | Deem et al. |
| 2007/0278103 A1 | 12/2007 | Hoerr et al. |
| 2008/0125772 A1 | 5/2008 | Stone et al. |
| 2008/0140002 A1 | 6/2008 | Ramzipoor et al. |
| 2008/0161801 A1 | 7/2008 | Steinke et al. |
| 2008/0188912 A1 | 8/2008 | Stone et al. |
| 2008/0188913 A1 | 8/2008 | Stone et al. |
| 2008/0262489 A1 | 10/2008 | Steinke |
| 2009/0018609 A1 | 1/2009 | DeLorenzo |
| 2009/0062873 A1 | 3/2009 | Wu et al. |
| 2009/0074828 A1 | 3/2009 | Alexis et al. |
| 2010/0076299 A1 | 3/2010 | Gustus et al. |
| 2010/0125239 A1 | 5/2010 | Perry et al. |
| 2010/0137952 A1 | 6/2010 | Demarais et al. |
| 2010/0160906 A1 | 6/2010 | Jarrard |
| 2010/0204560 A1 | 8/2010 | Salahieh et al. |
| 2010/0286684 A1 | 11/2010 | Hata et al. |
| 2010/0324472 A1 | 12/2010 | Wulfman |
| 2011/0092880 A1 | 4/2011 | Gertner |
| 2011/0104061 A1 | 5/2011 | Seward |
| 2011/0118598 A1 | 5/2011 | Gertner |
| 2011/0118600 A1 | 5/2011 | Gertner |
| 2011/0118726 A1 | 5/2011 | De La Rama |
| 2011/0178403 A1 | 7/2011 | Weng et al. |
| 2011/0207758 A1 | 8/2011 | Sobotka |
| 2011/0270238 A1 | 11/2011 | Rizq et al. |
| 2011/0306851 A1 | 12/2011 | Wang |
| 2011/0307034 A1 | 12/2011 | Hastings et al. |
| 2011/0319809 A1 | 12/2011 | Smith |
| 2012/0029496 A1 | 2/2012 | Smith |
| 2012/0029500 A1 | 2/2012 | Jenson |
| 2012/0029509 A1 | 2/2012 | Smith |
| 2012/0029511 A1 | 2/2012 | Smith |
| 2012/0029512 A1 | 2/2012 | Willard et al. |

FOREIGN PATENT DOCUMENTS

| | | |
|---|---|---|
| CN | 102271607 A | 7/2011 |
| DE | 102005041601 A1 | 4/2007 |
| DE | 102008048616 A1 | 4/2010 |
| EP | 558297 A2 | 9/1993 |
| EP | 647435 A1 | 4/1995 |
| EP | 634910 B1 | 8/1997 |
| EP | 868884 A2 | 10/1998 |
| EP | 1005838 A1 | 6/2000 |
| EP | 1053720 A1 | 11/2000 |
| EP | 1064886 A1 | 1/2001 |
| EP | 1181895 A2 | 2/2002 |
| EP | 1297795 A1 | 6/2002 |
| EP | 1264613 A2 | 12/2002 |
| EP | 1286625 A1 | 3/2003 |
| EP | 1332724 A1 | 8/2003 |
| EP | 866675 B1 | 10/2003 |
| EP | 1433448 A1 | 6/2004 |
| EP | 1442719 A1 | 8/2004 |
| EP | 1547537 A1 | 6/2005 |
| EP | 1634542 A1 | 3/2006 |
| EP | 1698296 A1 | 6/2006 |
| EP | 1709922 A1 | 10/2006 |
| EP | 1946712 A1 | 7/2008 |
| EP | 1961394 A2 | 8/2008 |
| EP | 1715798 B1 | 4/2009 |
| EP | 2092957 A1 | 8/2009 |
| EP | 2208506 A1 | 7/2010 |
| EP | 2241279 A1 | 10/2010 |
| EP | 2329859 A1 | 6/2011 |
| GB | 2313062 A | 11/1997 |
| GB | 2453601 A | 4/2009 |
| JP | 2003-510126 A | 3/2003 |
| WO | WO 91/03207 A1 | 3/1991 |
| WO | WO 91/17731 A1 | 11/1991 |
| WO | WO 93/20747 A1 | 10/1993 |
| WO | WO 93/20770 A2 | 10/1993 |
| WO | WO 94/18896 A1 | 9/1994 |
| WO | WO 94/28809 A1 | 12/1994 |
| WO | WO 95/01751 A1 | 1/1995 |
| WO | WO 95/31142 A1 | 11/1995 |
| WO | WO 96/34559 A1 | 11/1996 |
| WO | WO 97/03604 A1 | 2/1997 |
| WO | WO 97/17104 | 5/1997 |
| WO | WO 97/20510 A1 | 6/1997 |
| WO | WO 97/32532 A1 | 9/1997 |
| WO | WO 97/40760 A1 | 11/1997 |
| WO | WO 97/45156 A2 | 12/1997 |
| WO | WO 98/18393 A1 | 5/1998 |
| WO | WO 98/34565 A1 | 8/1998 |
| WO | WO 98/35638 A1 | 8/1998 |
| WO | WO 98/40023 A1 | 9/1998 |
| WO | WO 99/00060 | 1/1999 |
| WO | WO 99/16370 A1 | 4/1999 |
| WO | WO 99/21608 A1 | 5/1999 |
| WO | WO 99/34741 A1 | 7/1999 |
| WO | WO 99/44522 A1 | 9/1999 |
| WO | WO 00/10475 A1 | 3/2000 |
| WO | WO 00/51513 A1 | 9/2000 |
| WO | WO 00/59394 A1 | 10/2000 |
| WO | WO 00/62727 A1 | 10/2000 |
| WO | WO 00/64387 A1 | 11/2000 |
| WO | WO 00/69376 A1 | 11/2000 |
| WO | WO 00/72909 A1 | 12/2000 |
| WO | WO 01/22897 A1 | 4/2001 |
| WO | WO 01/37746 A1 | 5/2001 |
| WO | WO 01/87172 A1 | 5/2001 |
| WO | WO 01/87154 A1 | 11/2001 |
| WO | WO 01/95820 A1 | 12/2001 |
| WO | WO 02/28475 A1 | 4/2002 |
| WO | WO 02/39915 A1 | 5/2002 |
| WO | WO 02/058549 A1 | 8/2002 |
| WO | WO 02/080766 A2 | 10/2002 |
| WO | WO 02/087679 | 11/2002 |
| WO | WO 02/089686 | 11/2002 |
| WO | WO 03/077781 A1 | 9/2003 |
| WO | WO 2004/047659 A2 | 6/2004 |
| WO | WO 2004/049976 A1 | 6/2004 |
| WO | WO 2004/064606 A2 | 8/2004 |
| WO | WO 2004/069300 A2 | 8/2004 |
| WO | WO 2004/076146 A2 | 9/2004 |
| WO | WO 2004/098694 A1 | 11/2004 |
| WO | WO 2004/105807 A2 | 12/2004 |
| WO | WO 2005/007000 A1 | 1/2005 |
| WO | WO 2005/037070 A2 | 4/2005 |
| WO | WO 2005/074829 A1 | 8/2005 |
| WO | WO 2006/041881 A2 | 4/2006 |
| WO | WO 2006/105121 A2 | 10/2006 |
| WO | WO 2006/116198 A2 | 11/2006 |
| WO | WO 2007/011634 A1 | 1/2007 |
| WO | WO 2007/014063 A2 | 2/2007 |
| WO | WO 2007/047870 A2 | 4/2007 |
| WO | WO 2007/113865 A1 | 10/2007 |
| WO | WO 2007/135431 A2 | 11/2007 |
| WO | WO 2007/146215 A2 | 12/2007 |
| WO | WO 2008/003058 A2 | 1/2008 |
| WO | WO 2008/009972 A2 | 1/2008 |
| WO | WO 2008/010150 A2 | 1/2008 |
| WO | WO 2008/036281 A2 | 3/2008 |
| WO | WO 2008/049084 A2 | 4/2008 |
| WO | WO 2008/061152 A2 | 5/2008 |
| WO | WO 2008/102363 | 8/2008 |
| WO | WO 2009/036471 A1 | 3/2009 |
| WO | WO 2009/082635 A1 | 7/2009 |
| WO | WO 2009/088678 A1 | 7/2009 |
| WO | WO 2009/113064 A2 | 9/2009 |
| WO | WO 2009/121017 A1 | 10/2009 |
| WO | WO 2009/137819 A1 | 11/2009 |
| WO | WO 2010/042653 A1 | 4/2010 |
| WO | WO 2010/048007 A1 | 4/2010 |
| WO | WO 2010/056771 A1 | 5/2010 |
| WO | WO 2010/057043 A1 | 5/2010 |
| WO | WO 2010/070766 A1 | 6/2010 |
| WO | WO 2010/099207 A1 | 9/2010 |
| WO | WO 2010/120944 A2 | 10/2010 |
| WO | WO 2010/134503 A1 | 11/2010 |
| WO | WO 2011/055143 A2 | 5/2011 |
| WO | WO 2011/060339 A1 | 5/2011 |
| WO | WO 2011/126580 A2 | 10/2011 |

OTHER PUBLICATIONS

Brown et al., "Radiofrequency capacitive heaters: the effect of coupling medium resistivity on power absorption along a mouse leg" Phys Med Biol 1993, 38 1-12 (abstract).

Cardiovascular Technologies, Inc., "Heated Balloon Device Technology" [Presentation], 2007-2008, 11 pages total. Retrieved from: <<http://www.cvtechinc.com/pr/presoCVT_Heated_Balloon_Tech.pdf>>.

Carrington, "Future of CVI: Its All About the Plaque." Diagnostic Imaging Special Edition Forum [online] [retrieved on Sep. 3, 2003] Retreived from the Internet:,http://dimag.com/specialedition/cardiacimg.shtml> 5 pages total.

Cimino, "Preventing Plaque Attack", [online] [retrieved on Sep. 3, 2003] Retrieved from the Internet: <http://Masshightech.com/displayarticledetail.ap?art_id=52283&cat_id=10>, 3 pages total.

Dahm et al, "Relation of Degree of Laser Debulking of In-Stent Restenosis as a Predictor of Restenosis Rate", *Am J Cardiol*, 2002; 90(1): 68-70.

De Korte et al., "Characterization of Placque Components with Intravascular Ultrasound Elastography in Human Femoral and Coronary Arteries In Vitro," Circulation 2000;102:617-623.

Durney C., et al., Radiofrequency Radiation Dosimetry Handbook (with table of contents), Oct. 1986, 4th ed., 7 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/handbook/home.htm.

Fournier-Desseux et al. "Assessment of 1-lead and 2-lead electrode patterns in electrical impedance endotomography", Physiol. Meas. (2005) 26:337-349.

Fujimori et al., "Significant Prevention of In-Stent Restenosis by Evans Blue in Patients with Acute Myocardial Infarction", Abstract #2925, *AHA* (2002), 1 page total.

Fujita, "Sarpogrelate, An Antagonist of 5-HT$_{2a}$ Receptor Treatment Reduces Restenosis After Coronary Stenting", Abstract #2927, *AHA* (2002), 1 page total.

Gabriel C, et al., Compilation of the Dielectric Properties of Body Tissues at RF and Microwave Frequencies (with table of contents), Jun. 1996, 17 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Report/Report.html.

Gabriel C, et al., Compilation of the Dielectric Properties of Body Tissues at RF and Microwave Frequencies, Appendi04-10-2009 A, Jun. 1996, 21 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009.A/Appendi04-10-2009 A.html.

Gabriel C, et al., Compilation of the Dielectric Properties of Body Tissues at RF and Microwave Frequencies, Appendi04-10-2009 C, Jun. 1996, 6 pages, Armstrong Laboratory (AFMC) Occupational and Environmental Health Directorate Radiofrequency Radiation Division, USAF School of Aerospace Medicine, Aerospace Medical Division (AFSC), Brooks Air Force Base, http://www.brooks.af.mil/AFRL/HED/hedr/reports/dielectric/Appendi04-10-2009 .C/Appendi04-10-2009 C.html.

Gregory et al., "Liquid Core Light Guide for Laser Angioplasty", *Journal of Quantum Electronics*, vol. 26, No. 12, (Dec. 1990), pp. 2289-2296.

Intraluminal, Product description [online] [retrieved on Sep. 3, 2003] Retrieved from the Internet: http://www.intraluminal.com/products/inde04-10-2009 .html> 1 page total.

Kaplan et al., "Healing after arterial dilatation with radiofrequency thermal and nonthermal balloon angioplasty systems," J Invest Surg. Jan.-Feb. 1993;6(1):33-52.

Kolata, "New Studies Question Value of Opening Arteries", New York Times [online] [retrieved on Jan. 25, 2005]. Retrieved from the Internet: <http://nytimes.com/2004/03/21/health/21HEAR.html?ei=5070&en=641bc03214e&e04-10-2009 =11067>, 5 pages total.

Konings M K, et al., "Development of an Intravascular Impedance Catheter for Detection of Fatty Lesions in Arteries," IEEE Transactions on Medical Imaging, vol. 51, No. 4, Apr. 2004.

Kurtz et al., "Lamellar Refractive Surgery with Scanned Intrastromal Picosecond and Femtosecond Laser Pulses in Animal Eyes", *J Refract Surg*, vol. 14, (Sep./Oct. 1998), pp. 541-548.

Lightlab Imaging Technology, "Advantages of OCT", [online] [retrieved on Sep. 3, 2003]. Retrieved from the Internet: <http:www.lightlabimaging.com/advantage.html> 2 pages total.

Lightlab Imaging Technology, "Image Gallery", [online] [retrieved on Sep. 3, 2003]. Retrieved from the Internet: <http:lightlabimaging.com/gallery/cvpstill.html> 4 pages total.

Lightlab Imaging Technology, "LightLab Imaging Starts US Cardiology Clinical Investigations", LightLab Company Press Release, [online] [retrieved on Sep. 3, 2003]. Retrieved from the Internet: <http://www.lighlabimaging.com/press/cardtrails.html> 2 pages total.

Lightlab Imaging Technology, "LightLab Sees Bright Prospects for Cardiac Application of Oct Technology" *The Graysheet Medical Devices Diagnostics & Instrumentation*, vol. 27, No. 35, (Aug. 27, 2001) [online] [retrieved on Sep. 3, 2003]. Retrieved from the Internet: <http://www.lighlabimaging.com/press/graysheet.html> 1 page total.

Lightlab Imaging Technology, "What is OCT?", [online] [retrieved on Sep. 3, 2003]. Retrieved from the Internet: <http:lightlabimaging.com/oct.html.> 2 pages total.

Lightlab Imaging Technology, "Why use OCT?", [online] [retrieved on Sep. 3, 2003]. Retrieved from the Internet: <http:lightlabimaging.com/whyoct.html> 2 pages total.

Lima et al., "Efficacy and Safety of Oral Sirolimus to Treat and Prevent In-Stent Restenosis: A Pilot Study Results", Abstract #2929,*AHA* (2002), 1 page total.

Lima et al., "Systemic Immunosuppression Inhibits In-Stent Coronary Intimal Proliferation in Renal Transplant Patients", Abstract #2928, *AHA* (2002), 1 page total.

MIT Techtalk, "Laser Catheter to Aid Coronary Surgery", Jan. 9, 1991 [online] [retrieved on Feb. 7, 2005]. Retrieved from the Internet: <http://web.mit.edu/newsoffice/tt/1991/jan09/24037.html> 4 pages total.

Morice et al., "A Randomized Comparison of a Sirolimus-Eluting Stent With a Standard Stent for Coronary Revascularization", *N. Engl J Med*, Jun. 6, 2002; 346(23): 1773-1779.

Müller et al., "Effectiveness and Safety of Ultrasonic Atherosclerotic Plaque Ablation: In Vitro Investigation", *CardioVas. Intervent. Radiol.*, 1993; 16: 303-307.

Nair A, et al., "Regularized Autoregressive Analysis of Intravascular Ultrasound Backscatter: Improvement in Spatial Accuracy of Tissue Maps," IEEE Transactions on Ultrasonics, Ferroelectrics, and Frequency Control, vol. 51 No. 4, Apr. 2004.

Popma et al., "Chapter 38—Percutaneous Coronary and Valvular Intervention", Heart Disease: A Te04-10-2009 tbook of Cardiovascular Medicine, 6th ed., (2001) W.B> Saunders Company, pp. 1364-1405.

Romer et al., "Histopathology of Human Coronary Atherosclerosis by Quantifying Its Chemical Composition with Raman Spectroscopy," Circulation 1998; 97:878-885.

Scheller, "Intracoronary Paclitaxel Added to Contrast Media Inhibits In-Stent Restenosis of Porcine Coronary Arteries", Abstract #2227, AHA (2002), 2 pages total.

Shaffer, "Scientific Basis of Laser Energy", Clin Sports Med 2002; 21(4):585-598.

Shmatukha A V, et al., "MRI temperature mapping during thermal balloon angioplasty," Phys Med Biol 51, 2006; N163-N171.

Slager et al., "Vaporization of Atherosclerotic Placques by Spark Erosion," J Am Coll Cardiol, Jun. 1985; 5:1382-1386.

Stiles et al., "Simulated Characterization of Atherosclerotic Lesions in the Coronary Arteries by Measurement of Bioimpedance," IEEE Transactions On Biomedical Engineering, (Jul. 2003), 5(4): 916-921.

Süselbeck et al. "Intravascular electric impedance spectroscopy of atherosclerotic lesions using a new impedance system", Basic Res Cardiol 2005; 100:446-452.

Suselbeck T, et al., "In vivo intravascular electrical impedance spectroscopy using a new catheter with integrated microelectrodes," Basic Res Cardiol 2005; 100:28-34.

Van Den Berg, "Light Echoes Image the Human Body", *OLE*, Oct. 2001, pp. 35-37.

Volcano Therapeutics, "Product—Functional Measurement", [online] [retrieved on Sep. 3, 2003]. Retrieved from the Internet: <http://www.volcanotherapeutics.com/pages/products/functional_measurement-us.html> 2 pages total.

Scheller et al., "Potential Solutions to the Current Problem: Coated Balloon," EuroIntervention, Aug. 2008; 4 Suppl C: C63-66.

Tepe et al., "Local Delivery of Paclitaxel to Inhibit Restenosis During Angioplasty of the Leg," N Engl J Med, Feb. 14, 2008; 358(7): 689-699; retrieved from the Internet: <<http://content.nejm.org/cgi/reprint/358/7/689.pdf>>.

Examiners Report of Canadian Patent Application No. 2,539,026, mailed Feb. 6, 2012, 4 pages total.

Office Action issued in Chinese Patent Application No. 200480030163.9, mailed Jan. 16, 2009, 8 pages total.

Office Action issued in Chinese Patent Application No. 200480030163.9, mailed Mar. 28, 2008, 7 pages total.

Office Action issued in Chinese Patent Application No. 200480030163.9, mailed Aug. 31, 2007, 8 pages total.

Office Action issued in Chinese Patent Application No. 200480030163.9, mailed Jul. 31, 2009, 5 pages total.

Supplementary Partial European Search Report of Application No. 04816863.7, mailed May 8, 2009, 7 pages total.

Office Action issued in European Application No. 04816863.7, mailed Jun. 4, 2010, 5 pages total.

Office Action issued in European Application No. 04816863.7, mailed Dec. 5, 2011, 4 pages total.

Office Action issued in European Application No. 04816863.7, mailed Jan. 22, 2010, 6 pages total.

Formal Inquiry issued in Japanese Patent Application No. 2006-526351, mailed Jan. 17, 2012, 5 pages total.
Notice of the Reason for Refusal issued in Japanese Patent Application No. 2006-526351, mailed Apr. 27, 2010, 6 pages total.
Final Decision of Rejection issued in Japanese Patent Application No. 2006-526351, mailed Jan. 18, 2011, 4 pages total.
European Search Report and Search Opinion of EP Patent Application No. 12151957.3, mailed Apr. 16, 2012, 8 pages total.
Office Action issued in Chinese Patent Application No. 200680016424.0, mailed Apr. 13, 2010, 10 pages total.
European Search Report and Search Opinion of EP Patent Application No. 06748830.4, mailed Nov. 16, 2009, 12 pages total.
Partial European Search Report of EP Patent Application No. 11191822.3, mailed Mar. 19, 2012, 7 pages total.
Office Action issued in Chinese Patent Application No. 201110031923.X, mailed Nov. 17, 2011, 16 pages total.
Office Action issued in Chinese Patent Application No. 201110031923.X, mailed May 22, 2012, 10 pages total.
Examiner's First Report of Australian Patent Application No. 2007310988, mailed May 23, 2012, 4 pages total.
European Search Report and Search Opinion of EP Patent Application No. 07844421.3, mailed Jan. 4, 2010, 15 pages total.
European Search Report and Search Opinion of EP Patent Application No. 12155447.1, mailed May 10, 2012, 6 pages total.
European Search Report and Search Opinion of EP Patent Application No. 07844417.1, mailed Nov. 5, 2009.
European Search Report and Search Opinion of EP Patent Application No. 12154120.5, mailed May 8, 2012, 8 pages total.
European Search Report and Search Opinion of EP Patent Application No. 07844424.7, mailed Nov. 11, 2009, 11 pages total.
Partial European Search Report of EP Patent Application No. 12154069.4, mailed May 10, 2012, 5 pages total.
International Search Report and Written Opinion of PCT Application No. PCT/US2009/064465, mailed Jan. 13, 2010, 13 pages total.
International Search Report of PCT Application No. PCT/US09/57728, mailed Nov. 30, 2009, 10 pages total. (2410PC).
International Search Report and Written Opinion of PCT/US2010/034789, mailed Jul. 9, 2010, 13 pages total.
International Search Report and Written Opinion of PCT/US2011/00661, mailed Nov. 18, 2011, 14 pages total.

SELECTIVE ACCUMULATION OF ENERGY WITH OR WITHOUT KNOWLEDGE OF TISSUE TOPOGRAPHY

CROSS-REFERENCES TO RELATED APPLICATIONS

The present application claims the benefit under 35 USC 119(e) of U.S. Provisional Application No. 61/115,344 filed Nov. 17, 2008; the full disclosure of which is incorporated herein by reference in its entirety.

This application is related to U.S. application Ser. No. 11/975,474, filed on Oct. 18, 2007, entitled "Inducing Desirable Temperature Effects on Body Tissue"; U.S. application Ser. No. 11/975,383, filed on Oct. 18, 2007, and entitled "System for Inducing Desirable Temperature Effects on Body Tissues", U.S. patent application Ser. No. 11/122,263, filed on May 3, 2005, entitled "Imaging and Eccentric Atherosclerotic Material Laser remodeling and/or Ablation Catheter", and U.S. Provisional Application No. 61/099,155, filed on Sep. 22, 2008, entitled "Inducing Desirable Temperature Effects On Body Tissue Using Alternate Energy Sources", the full disclosures of which are incorporated herein by reference.

STATEMENT AS TO RIGHTS TO INVENTIONS MADE UNDER FEDERALLY SPONSORED RESEARCH AND DEVELOPMENT

Not Applicable

BACKGROUND OF THE INVENTION

The present invention is generally related to medical devices, systems, and methods for heating body tissue. In exemplary embodiments, the invention provides catheter-based treatment for heating body tissue with energy that selectively accumulates in a desired type of tissue, particularly diseased tissue, with or without knowing the tissue topography a-priori.

Balloon angioplasty and other catheters often are used to open arteries that have been narrowed due to atherosclerotic disease. The trauma associated with balloon dilation can impose significant injury, so that the benefits of balloon dilation may be limited in time. Stents are commonly used to extend the beneficial opening of the blood vessel. Restenosis or a subsequent narrowing of the body lumen after stenting has occurred in a significant number of cases.

More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) which may also improve the procedural angioplasty success rates.

While drug eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches. More recently, still further disadvantages of dilation have come to light. These include the existence of vulnerable plaque, which can rupture and release materials that may cause myocardial infarction or heart attack.

In light of the above, it would be advantageous to provide methods and systems for inducing vasodilation in artery tissue and remodeling of the lumens of the body. It would further be desirable to avoid significant cost or complexity while providing structures which could remodel body lumens without having to resort to the trauma of extreme dilation, and to allow the opening of blood vessels and other body lumens which are not suitable for stenting.

BRIEF SUMMARY OF THE INVENTION

In a first aspect, embodiments of the present invention provide a method for heating a body tissue region adjacent a body lumen, the region having both a first tissue type and a second tissue type. The method includes positioning an energy delivery portion of a catheter body within the lumen adjacent the body tissue region to be heated, determining a pulse characteristic in response to a thermal property of the first tissue type and applying pulsed energy with the pulse characteristic from the energy delivery portion so as to therapeutically treat the second tissue type within the body tissue region by drawing heat from the first tissue type at a rate that avoids significant thermal damage to the first tissue type while building-up heat in the second tissue type.

In another aspect, embodiments of the present invention provide a catheter system for heating a body tissue region adjacent a body lumen, the region having both a first tissue type and a second tissue type. The system includes an elongate flexible catheter body having a proximal end and a distal end with an axis therebetween, an energy delivery portion proximate the distal end, an energy source coupled to the energy delivery portion and a processor coupled to the energy source, the processor configured to control a pulse characteristic of pulsed energy transmitted from the energy source to the energy delivery portion so as to therapeutically treat the second tissue type within the body tissue region by drawing heat from the first tissue type at a rate that avoids significant thermal damage to the first tissue type while building-up heat in the second tissue type.

In many embodiments, the pulsed energy preferentially heats the second tissue type more than the first tissue type, the preferential heating induced at least in part by one or more of the following group of characteristics of the second tissue type: lower thermal conduction than a thermal conduction of the first tissue type, lower specific heat capacity than a specific heat capacity of the first tissue type, less innate blood perfusion than an innate blood perfusion of the first tissue type, and/or larger distance away from well-perfused areas than a distance between well-perfused areas and the first tissue type.

In many embodiments, most of the group of characteristics cause heat to be drawn from the first tissue type at a rate that avoids significant thermal damage to the first tissue type, while allowing heat to build up in the second tissue type.

In many embodiments, the pulsed energy is delivered at an average rate of 0.25 to 5 watts to the body tissue region.

In many embodiments, each pulse of the pulsed energy provides between 4 to 45 Joules to the body tissue region.

In many embodiments, wherein an average rate of pulsed energy delivered to the body tissue region is between about 0.1 and 10.0 times the rate of energy dissipation by the first tissue type.

In many embodiments, a time period between pulses allows the first tissue type to dissipate its heat adequately to avoid thermal damage to the first tissue type by the pulsed energy.

In many embodiments, the time period between pulses of energy is between 0.1 to 180 seconds.

In many embodiments, a thermal time constant for the first tissue type is approximately how long it will take a discrete volume of that given tissue to lose 63% of its heat while undergoing an exponential decay.

In many embodiments, the pulsed energy is delivered to the body tissue region over a duration of at least several first tissue type time constants, wherein the thermal time constant of the first tissue is proportional to a thermal conductivity of the first tissue type.

In many embodiments, the thermal conductivity of the second tissue type is twice that of the first tissue type.

In many embodiments, the energy source comprises a radio frequency (RF) energy source.

In many embodiments, the energy delivery portion comprises a radially expandable structure engaging a plurality of electrode surfaces against the body lumen, wherein the plurality of electrode surfaces against the body lumen complete a plurality of circuits comprising the first tissue type and the second tissue type and pulsed energy is delivered to the plurality of circuits.

In many embodiments, the energy source comprises a laser energy source.

In many embodiments, the energy delivery portion comprises at least one radially oriented window coupled to at least one optical conduit extending between the proximal end of the catheter body and the at least one window for transmission of pulsed laser energy to the body tissue region.

In many embodiments, the energy source comprises an ultrasound transmitter configured to deliver pulsed ultrasound energy to the body tissue region.

In many embodiments, the energy source comprises a microwave energy source including at least one microwave antenna configured to deliver pulsed microwave energy to the body tissue region.

DETAILED DESCRIPTION OF THE INVENTION

Figure 1:
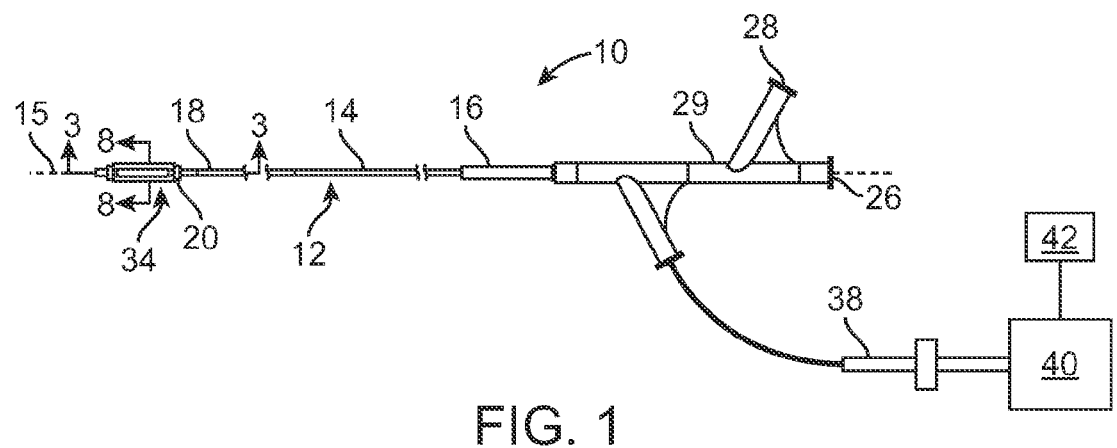
FIG. 1 schematically illustrates one embodiment of a catheter system for heating artery tissue.

Many therapies have been developed to replace or improve upon traditional balloon angioplasty and stents. Many of the devices described in the BACKGROUND OF THE INVENTION either cut, ablate, or vaporize diseased tissue in an artery. For example, laser devices vaporize plaque and flush it downstream. Atherectomy devices excise plaque and suck it out of the body. Cutting balloons incise the artery wall, damaging the tissue.

It would be advantageous to provide systems and devices that do not cut, ablate, or vaporize. Three modalities of treatment avoid these drawbacks, they include: cooling the tissue; non-ablative forms of direct molecular denaturing; and non-ablative heating. Cooling has been implemented using devices such as Boston Scientific's Cryo-cath. Direct molecular denaturing can be achieved with radiation—gamma rays, for instance. The present invention is directed to the remaining modality, non-ablative heating.

Some embodiments of the present invention generally provide devices, systems, and methods for heating artery tissue with diseased portions using selective accumulation of energy in the artery tissue with or without knowledge of tissue topography, discussed in more detail below. The invention will be particularly useful for remodeling materials along a partially occluded artery in order to open the artery lumen and increase blood flow. The devices, systems, and methods disclosed herein may be used in any artery, for example, the femoral, popliteal, coronary and/or carotid arteries. Devices for heating artery tissue have been disclosed in co-pending U.S. patent application Ser. Nos. 11/975,474, 11/975,383, 11/122,263 and U.S. Provisional Application No. 61/099,155, the full disclosures of which are incorporated herein by reference.

While the disclosure focuses on the use of the technology in the vasculature, the technology would also be useful for any luminal obstruction. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Some embodiments of the system will be able to treat tissue by gentle heating in combination with dilation of the artery. The heating of the vessel wall may be done before, during, and/or after dilation with the balloon, with dilation pressures which are at or significantly lower than standard, unheated angioplasty dilation pressures. For example, where balloon inflation pressures of 10-16 atmospheres may be appropriate for standard angioplasty dilation of a particular lesion, modified dilation treatments combined with gentle heating described herein may employ from 10-16 atmospheres or may be effected with pressures of 6 atmospheres or less, and possibly as low as 1 to 2 atmospheres. In case of calcification in the artery plaque, it may be more difficult to remodel and open the diseased artery, so the catheter may use a standard angioplasty balloon in combination with ultrasonic energy to break down the calcium and remodel and open the lumen.

The gentle heating energy added before, during, and/or after dilation of a blood vessel may increase dilation effectiveness while lowering complications. In some embodiments, such controlled heating with balloon dilatation may exhibit a reduction in recoil, providing at least some of the benefits of a stent-like expansion without the disadvantages of an implant. Benefits of gentle heating may be enhanced (and/or complications inhibited) by limiting heating of the adventitial layer below a deleterious response threshold. In many cases, such heating of the intima and/or media may be provided using heating times of less than about 10 seconds, often being less than 3 (or even 2) seconds. In other cases, very low power may be used for longer durations.

Heating of the body tissue involves the application of energy, typically in the form of RF, microwave and/or ultrasound energy, and the like. This energy will be controlled so as to limit a temperature of the body tissue. In some embodiments, the body tissue temperature range is from about 50° C. to about 90° C., depending on the energy applied and tissue type.

While the methods and devices described herein are not selective in tissue treatment of the blood vessel, the devices can be used for treatment of both concentric and eccentric atherosclerosis. This non selective treatment is a particular advantage because atherosclerosis may be eccentric relative to an axis of the blood vessel over 50% of the time, possibly in as much as (or even more than) 75% of cases.

While the present invention may be used in combination with stenting, the present invention is particularly well suited for increasing the open diameter of blood vessels in which stenting is not a viable option. Potential applications include treatment of diffuse disease, in which atherosclerosis is spread along a significant length of an artery rather than being localized in one area. The present invention may also find advantageous use for treatment of tortuous, sharply-curved vessels, as no stent need be advanced into or expanded within the sharp bends of many blood vessel. Still further advantageous applications include treatment along bifurcations (where side branch blockage may be an issue) and in the peripheral extremities such as the legs, feet, and arms (where crushing and/or stent fracture failure may be problematic).

The disclosed system includes at least an energy source and a catheter with an energy delivery portion configured for heating a body tissue region adjacent a body lumen, the region having both a first tissue type, such as healthy tissue, and a second tissue type, such as diseased tissue. The catheter may be similar to a balloon catheter commonly used to treat artery disease today, except for the addition of electrodes used for heating. Other embodiments may use transducers disposed on the balloon to apply ultrasound heating to the vessel wall or microwave antennas disposed on the balloon to apply microwave heating to the vessel wall. The energy source may be coupled to a processor to control a pulse characteristic of pulsed energy transmitted from the energy source to the energy delivery portion so as to therapeutically treat the tissue within the body treatment region without causing sufficient thermal damage to the body treatment region so as to induce a long-term occlusive response.

In use, the energy delivery portion of a catheter body is positioned within the lumen adjacent the body tissue region to be heated. A pulse characteristic is determined in response to a thermal property of the first tissue type, and the pulsed energy is applied with the pulse characteristic from the energy delivery portion so as to therapeutically treat the body tissue region.

FIG. 1 shows one embodiment of a catheter system 10 for heating artery tissue. The catheter system 10 includes a balloon catheter 12 having a catheter body 14 with a proximal end 16 and a distal end 18. Catheter body 14 is flexible and defines a catheter axis 15, and may include one or more lumens, such as a guidewire lumen 22 and an inflation lumen 24 (see FIG. 2). Still further lumens may be provided if desired for other treatments or applications, such as perfusion, fluid delivery, imaging, or the like. Catheter 12 includes an inflatable balloon 20 adjacent distal end 18 and a housing 29 adjacent proximal end 16. Housing 29 includes a first connector 26 in communication with guidewire lumen 22 and a second connector 28 in fluid communication with inflation lumen 24. Inflation lumen 24 extends between balloon 20 and second connector 28. Both first and second connectors 26, 28 may optionally comprise a standard connector, such as a Luer-Loc™ connector. A distal tip may include an integral tip valve to allow passage of guidewires, and the like.

Housing 29 also accommodates an electrical connector 38. Connector 38 includes a plurality of electrical connections, each electrically coupled to electrodes 34 via conductors 36. This allows the electrodes 34 to be easily energized, the electrodes often being energized by a controller 40 and energy source 42, such as bipolar or monopolar RF energy, microwave energy, ultrasound energy, or other suitable energy sources. In one embodiment, electrical connector 38 is coupled to an RF generator via a controller 40, with controller 40 allowing energy to be selectively directed to electrodes 38. When monopolar RF energy is employed, patient ground may (for example) be provided by an external electrode or an electrode on catheter body 14.

In some embodiments, controller 40 may include a processor or be coupled to a processor to control or record treatment. The processor will typically comprise computer hardware and/or software, often including one or more programmable processor unit running machine readable program instructions or code for implementing some or all of one or more of the methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an Ethernet, an internet, an intranet, or the like), and some or all of the code may also be transmitted between components of catheter system 10 and within processor via one or more bus, and appropriate standard or proprietary communications cards, connectors, cables, and the like will often be included in the processor. Processor will often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and will typically have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

Figure 2:
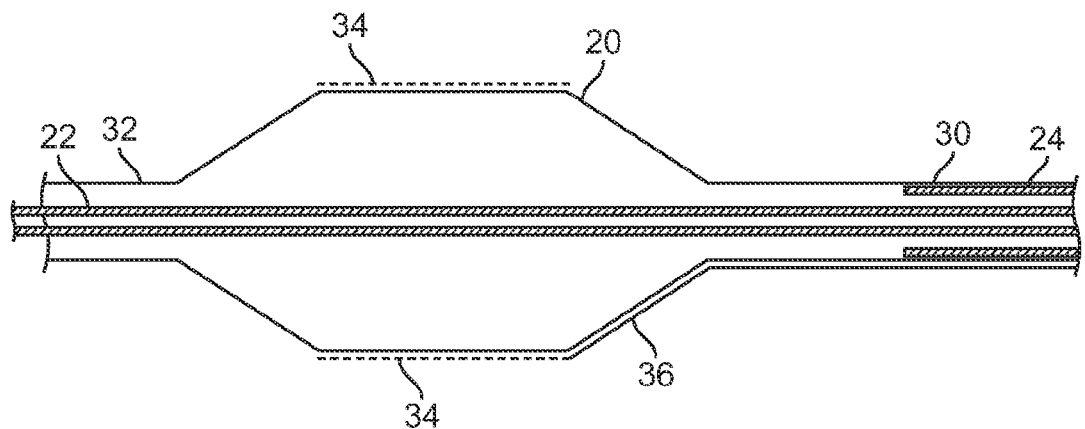
FIG. 2 illustrates one embodiment of a balloon for use in the catheter system of FIG. 1.

Balloon 20 is illustrated in more detail in FIG. 2. Balloon 20 generally includes a proximal portion 30 coupled to inflation lumen 24 and a distal portion 32 coupled to guidewire lumen 22. Balloon 20 expands radially when inflated with a fluid or a gas. In some embodiments, the fluid or gas may be non-conductive and/or cooled. In some embodiments, balloon 20 may be a low pressure balloon pressurized to contact the artery tissue. In other embodiments, balloon 20 is an angioplasty balloon capable of higher pressure to both heat the artery tissue and expand the artery lumen. Balloon 20 may comprise a compliant or non-compliant balloon having helical folds to facilitate reconfiguring the balloon from a radially expanded configuration to a low profile configuration, particularly for removal after use.

Electrodes 34 are mounted on a surface of balloon 20, with associated conductors 36 extending proximally from the electrodes. Electrodes 34 may be arranged in many different patterns or arrays on balloon 20. The system may be used for monopolar or bipolar application of energy. For delivery of monopolar energy, a ground electrode is used, either on the catheter shaft, or on the patients skin, such as a ground electrode pad. For delivery of bipolar energy, adjacent electrodes are axially offset to allow bipolar energy to be directed between adjacent circumferential (axially offset) electrodes. In other embodiments, electrodes may be arranged in bands around the balloon to allow bipolar energy to be directed between adjacent distal and proximal electrodes. In some embodiments, the electrodes 34 may be positioned internal of balloon 20. Electrodes 34 may be arranged in many different patterns or arrays on balloon 20. As mentioned previously, other embodiments may include ultrasound transducers or microwave antennas mounted on a surface of balloon 20.

The embodiments disclosed herein revolve around the concept of selective accumulation of energy in artery tissue with or without knowledge of tissue topography. This is accomplished by taking advantage of the differences in tissue properties between healthy tissue and diseased tissue. The preferential heating of the tissues with different properties can be accomplished without knowing the location or type the different tissues. If a first tissue type has a better thermal conductivity (k) than a second tissue type, it will conduct heat away more rapidly. If the second tissue type has a lower specific heat capacity ($c_p$) than the first tissue type, its temperature will increase more given the same amount of energy applied to the same mass (and volume, assuming relatively similar tissue density). If the first tissue type has denser vasculature, or is reliably in closer proximity to well-perfused areas, it will conduct heat away more rapidly than the second tissue type.

This present invention allows preferentially heating of a type of tissue that has one or more of the following characteristics:
Relatively poor (lower) thermal conduction,
Lower specific heat capacity,
Less innate blood perfusion, and/or
Relatively larger distance away from well-perfused areas.

In the case of diseased tissue, all of the above characteristics apply. The disease is generally comprised of lipidic fat-like diseased tissue and/or fibrous collagen-like tissue. Both of these tissues have a lower specific heat capacity and lower thermal conductivity than healthy vascular tissue, particularly media. Healthy vascular tissue also has more microvasculature, and is in closer proximity to well-perfused tissue, therefore healthy tissue can sink heat away more effectively, without the heat flux "backing up" like a traffic jam.

The key to taking advantage of this discrepancy in tissue properties is the following: Heat is applied or generated within the tissue at a rate commensurate with the thermal time constants of the tissues involved, possibly using a pulse width modulation (PWM) approach. During each "pulse", the same quantity of energy is delivered or generated regardless of the tissue type. Tissue topography may be unknown, therefore the same "treatment" is applied everywhere. However, in the diseased tissue, the temperature profile will be higher everywhere because it has a lower heat capacity. The diseased tissue will also retain its heat longer because it has lower thermal conductivity and therefore a longer thermal time constant. Thus, the healthy tissue will heat up slower and cool off faster, which is exactly what is desired for this particular application. The goal is to heat diseased tissue while not heating healthy tissue. The amount of time between pulses can then be tailored to allow the healthy tissue to cool and dissipate its heat adequately so as not to exceed a particular amount of thermal damage the healthy tissue.

Figure 3:
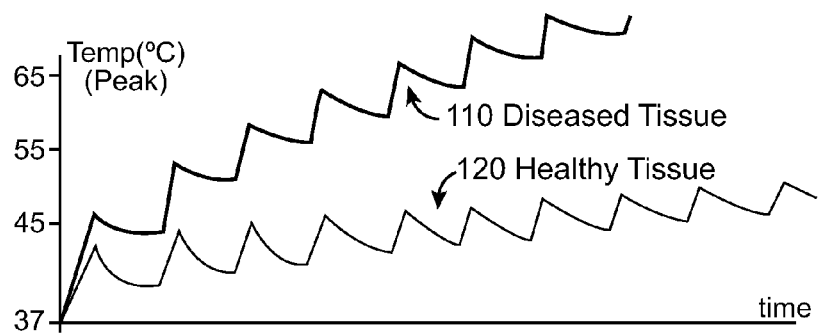
FIG. 3 shows what a temperature vs. time profile for heating both healthy tissue and diseased tissue at a constant pulsed rate of heat or energy.

FIG. 3 shows what a temperature vs. time profile for heating both healthy tissue 110 and diseased tissue 120 at a constant pulsed rate of heat or energy. The diseased tissue temperature will rise faster and cool slower than the healthy tissue, therefore accumulating heat and receiving treatment significantly more than healthy tissue.

Figure 4:
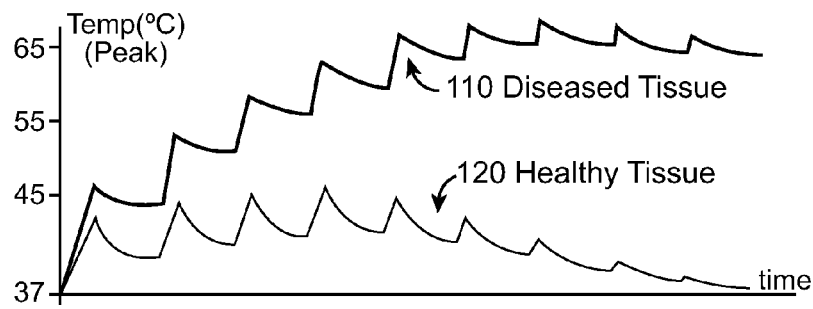
FIG. 4 shows another a temperature vs. time profile for tissue having both healthy tissue and diseased tissue in which the heat or energy is applied at different rates.

FIG. 4 shows another a temperature vs. time profile for tissue having both healthy tissue and diseased tissue in which the heat or energy is applied at different rates. The figure shows it is possible to initially apply or generate heat faster (at the beginning of the treatment) in order to ramp up the tissue temperature more quickly. This could be done with power modulation or PWM with a variable pulse width. The purpose of this would be to heat the tissue quickly and then allow the healthy tissue to dissipate heat between pulses, which would decrease the total treatment time required to achieve (and possibly soak at) a certain temperature.

Time Constant:

$$t = RC = \left(\frac{l}{n}k\right)(mc_p),$$

where healthy $t \approx 7$ s and diseased $t \approx 14$ s.

Heat Capacity:

Media $c_p \approx 3.9$

Adventitia $c_p \approx 3.1$

Fat $c_p \approx 2.4$

Thermal Conductivity:

Media $k \approx 0.59$

Adventitia $k \approx 0.49$

Fat $k \approx 0.20$

The "TIME CONSTANT" above is the thermal time constant. This is approximately how long it will take a discrete volume of that given tissue to lose 63% of its heat (and therefore temperature) while undergoing an exponential decay. The thermal time constant is directly proportional to the thermal conductivity. Therefore, because there is approximately a 2:1 ratio between the thermal conductivity of fatty diseased tissue and healthy media tissue, there is also a 2:1 ratio between their time constants.

The thermal time constant for healthy media tissue was estimated to be 7 seconds based upon a treatment volume of 32 mm$^3$, a thermal conductivity of 0.5 W/m/K, a thermal front cross-sectional area of 32 mm$^2$, and a specific heat capacity of 3.6 J/g/K. In this case, one would want to deliver an appropriate therapeutic dose of energy over a duration of at least several time constants, e.g. 35 seconds, 70 seconds, etc.

Figure 5:
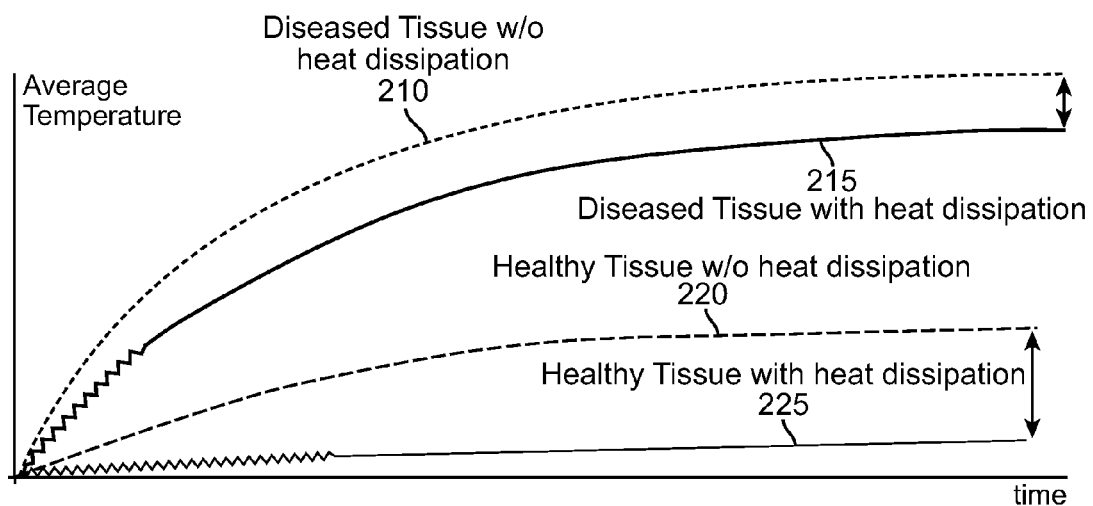
FIG. 5 shows heat dissipation's effect on temperature.

FIG. 5 shows heat dissipation's effect on temperature versus time. Because thermal dissipation will happen according to an exponential decay, the rate of cooling will vary nonlinearly with time. So, the period has to be selected appropriately in conjunction with the power and duty cycle. The power and the heat capacity, neglecting heat dissipation, will determine the rate of temperature increase during heating. The combination of power, duty cycle, heat capacity, and the rate of continuous heat dissipation, will determine the average rate of temperature change. Diseased tissue 210 and healthy tissue 220 both have higher average temperatures without heat dissipation than diseased tissue 215 and healthy tissue 225 with heat dissipation.

The important thing to note about FIG. 5 is that the average power (average energy per time) has to be low enough that the rate of heat dissipation is significant in comparison. In other words, if we were to assume that healthy vessel tissue in a certain geometry can effectively dissipate energy at a rate of 2 Joules per second (2 Watts), then the average rate of energy application needs to be on this order of magnitude as well, in order for the effect to be significant.

This is the main crux of the invention—applying energy at an average rate commensurate with the thermal time constants involved such that significant differences in the tissues' thermal properties can be leveraged to our advantage.

Figure 6:
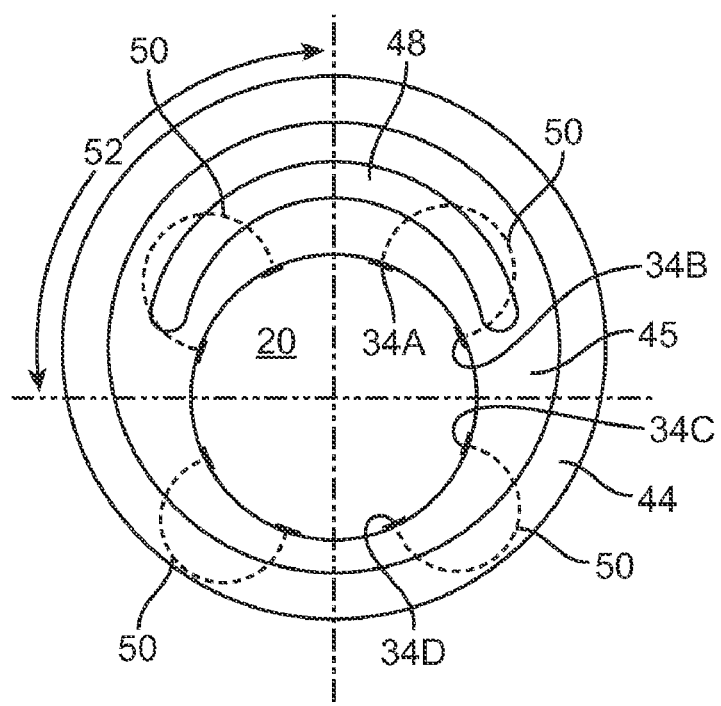
FIG. 6 schematically illustrates one embodiment of balloon catheter system for use for bipolar treatment of tissue in a leg FIG. 7 schematically illustrates one embodiment of balloon catheter system for use for monopolar treatment of tissue in a leg.

FIG. 6 schematically illustrates bipolar treatment of tissue with the system 10. Balloon 20 having electrode pairs 34A and 34B is positioned within an artery lumen having fatty disease/necrotic core 48, fibrous disease/fibrous cap 44, healthy tissue 45. Treatment is done to healthy tissue 45 and the fatty disease/necrotic core 48, fibrous disease/fibrous cap 44 by pulsed energy between electrode pairs 34A and 34B. The electrode pairs may be any electrode pairs on the balloon, for example, in some embodiments, the electrode pairs may be 34A and 34C, or 34A and 34D, or any combination of 34A-34D. This arrangement creates an energy path 50 through the tissue that delivers energy or heat ("tissue remodeling energy") to the artery tissue between the electrode pairs ("remodeling zones"). Using different combinations of electrode pairs may reduce or eliminate gaps between the remodeling zones by using overlapping pairs. Using electrode pairs with bipolar energy may avoid some potential issues of the monopolar approach. Diseased artery tissue 48 has a higher electrical resistivity than healthy artery tissue 45. By using pairs of electrodes 34A, 34B in a bipolar system, the energy path 50 will go through the healthy tissue, diseased tissue, or a combination of both healthy and diseased tissues between the electrode pairs. Any number of electrode pairs may be used in different patterns or arrays.

Figure 7:
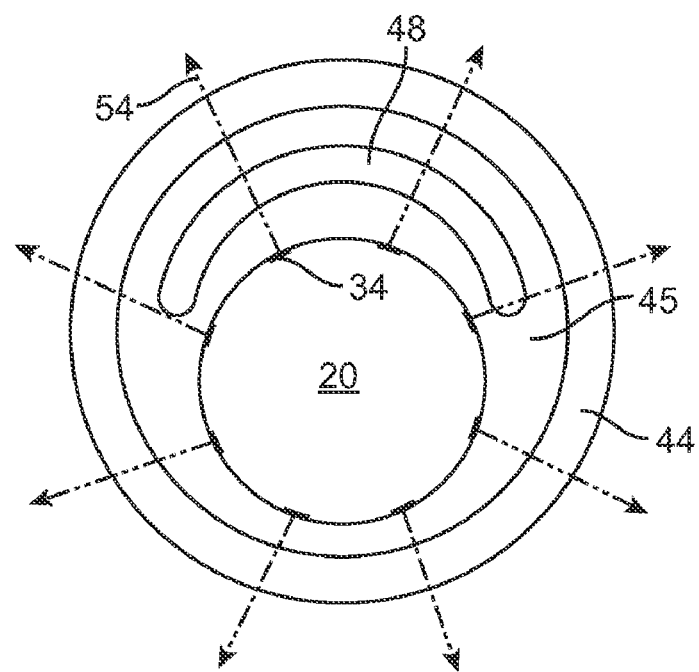

FIG. 7 schematically illustrates bipolar treatment of tissue with the system 10. Balloon 20 having electrode pairs 34A and 34B is positioned within an artery lumen having fatty disease/necrotic core 48, fibrous disease/fibrous cap 44, healthy tissue 45 and one or more electrical grounds (not shown) are used, such as positioned on the patients skin. When power is applied to the multiple monopolar electrodes 34 arranged around the circumference of the artery lumen, energy 54 is directed radially outward through the artery wall and treats both diseased and healthy artery tissue.

Figure 8A:
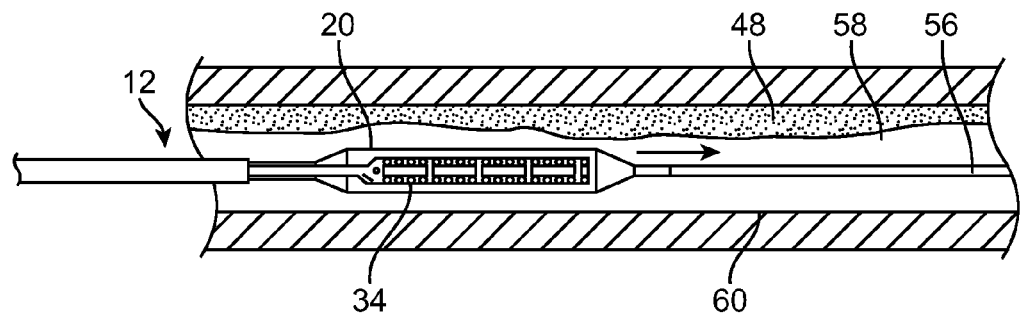
FIGS. 8A-8C illustrate a method of using a balloon catheter system treating artery tissue.
Figure 8B:
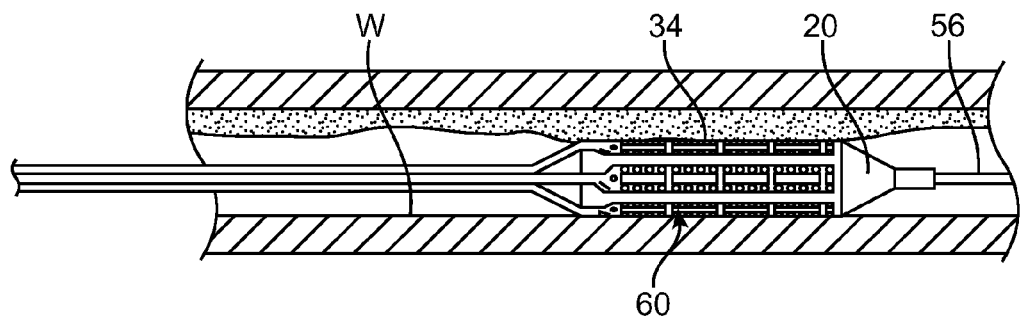
Figure 8C:
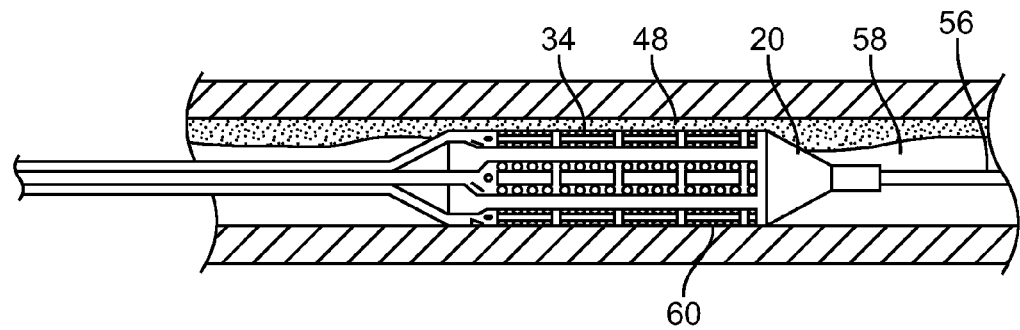

The use of catheter system 10 for treating tissue by pulsed energy can be understood with reference to FIGS. 8A-8C. As seen in FIG. 8A, accessing of a treatment site will often involve advancing a guidewire 56 within a blood vessel 58 at a target region of diseased tissue 48. Location of balloon 20 may be facilitated by radiopaque markers or by radiopaque structure (or corresponding radiopaque markers placed on or near) balloon 20, and/or by the use of radiopaque electrodes 34. Guidewire 56 may be positioned under fluoroscopic (or other) imaging.

Catheter 12 is advanced distally over guidewire 56 and positioned adjacent to atherosclerotic material 48. Balloon 20 expands radially within the lumen of the blood vessel so that electrodes 34, or electrodes 34A and 34B, radially engage artery tissue. As diseased tissue 48 may be distributed eccentrically about catheter 12, electrodes 34 may engage diseased tissue 48, healthy tissue 60, or a combination of both tissues.

As discussed above, electrodes 34 are positioned circumferentially around the balloon 20. Pulsed energy is directed to electrodes 34, or adjacent pairs of electrodes 34A and 34B, treating both diseased tissue 48 and the healthy tissue 60. The controller 40 may provide pulsed energy to energize the electrodes with about 0.25 to 5 Watts average power for 0.1 to 180 seconds, or with about 4 to 45 Joules. The power and duration are calibrated to be less than enough to cause severe damage, and particularly less than enough to ablate tissue within a blood vessel.

Referring now to FIG. 8C, as described above, balloon 20 may be an angioplasty balloon that combines heating with opening the artery lumen, such that the heat is preferentially delivered to the diseased tissue 48, for example to mildly heat a cap structure (to induce thickening of the cap and make the plaque less vulnerable to rupture) and/or heat a lipid-rich pool of the vulnerable plaque (so as to remodel, denature, melt, shrink, and/or redistribute the lipid-rich pool), while the healthy tissue 60 dissipates the heat without damage.

In some embodiments, balloon 20 may be repeatedly contracted, axial movement of the catheter 12 employed to reposition balloon 20, with subsequent expansion of balloon 20 at each of a plurality of treatment locations along diseased tissue.

While generally described herein with reference to the vasculature, embodiments of the catheter devices, systems, and methods described herein may also find applications in the lumens of other vessels of the human anatomy having tissue types with different tissue properties, as discussed above. The anatomical structure into which the catheter is placed may be for example, the esophagus, the oral cavity, the nasopharyngeal cavity, the auditory tube and tympanic cavity, the sinus of the brain, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal, as well as the arterial system, the venous system, and/or the heart.

While the exemplary embodiments have been described in some detail, by way of example and for clarity of understanding, those of skill in the art will recognize that a variety of modifications, adaptations, and changes may be employed. Hence, the scope of the present invention should be limited solely by the claims.

What is claimed is:

1. A method for heating a body tissue region adjacent a body lumen, the region having both a first tissue type and a second tissue type, the method comprising:

positioning an energy delivery portion of a catheter within the lumen adjacent the body tissue region to be heated, wherein the energy delivery portion comprises a radially expandable structure having a plurality of electrodes thereon;

expanding the radially expandable structure within the body lumen so as to radially engage the body lumen with the plurality of electrodes, wherein the plurality of electrodes engaged against the body lumen complete a plurality of circuits, wherein at least some of the circuits include a first tissue type and a second tissue type while other circuits include a first tissue type without the second tissue type;

determining a pulse characteristic in response to a thermal property of the first tissue type;

applying pulsed electrical energy with the pulse characteristic from the energy delivery portion through the plurality of circuits without identifying which of the plurality of circuits include the second tissue type so as to heat both the first and second tissue type by thermal conduction, thereby therapeutically treating the second tissue type within the body tissue region by drawing heat from the first tissue type at a rate that avoids significant thermal damage to the first tissue type while building-up heat in the second tissue type; and controlling the pulse characteristic in response to differing values of the thermal property of the first tissue type during application of pulsed electrical energy.

2. The method of claim 1, wherein the pulsed energy preferentially heats the second tissue type more than the first tissue type, the preferential heating induced at least in part by one or more of the following group of characteristics of the second tissue type: lower thermal conduction than a thermal conduction of the first tissue type, lower specific heat capacity than a specific heat capacity of the first tissue type, less innate blood perfusion than an innate blood perfusion of the first tissue type, and/or larger distance away from well-perfused areas than a distance between well-perfused areas and the first tissue type so that applying the pulsed energy with the pulse characteristic through the at least some circuits the first and second tissue types therapeutically heat the second tissue type while avoiding significant thermal damage to the first tissue and applying the same pulsed energy with the pulse characteristic through the other circuits including the first tissue type without the second tissue type so as to avoid significant thermal damage to the first tissue type.

3. The method of claim 2, wherein most of the group of characteristics cause heat to be drawn from the first tissue type at a rate that avoids significant thermal damage to the first tissue type, while allowing heat to build up in the second tissue type.

4. The method of claim 1, wherein the pulsed energy is delivered at an average rate of 0.25 to 5 watts to the body tissue region.

5. The method of claim 1, wherein each pulse of the pulsed energy provides between 4 to 45 Joules to the body tissue region.

6. The method of claim 1, wherein an average rate of pulsed energy delivered to the body tissue region is between about 0.1 and 10.0 times a rate of energy dissipation by the first tissue type.

7. The method of claim 1, wherein a time period between pulses allows the first tissue type to dissipate its heat adequately to avoid thermal damage to the first tissue type by the pulsed energy.

8. The method of claim 1, wherein the time period between pulses of energy is between 0.1 to 180 seconds.

9. The method of claim 1, wherein a thermal time constant for the first tissue type is approximately how long it will take a discrete volume of that given tissue to lose 63% of its heat while undergoing an exponential decay.

10. The method of claim 1, wherein the pulsed energy is delivered to the body tissue region over a duration of at least several differing first tissue type time constants, wherein the thermal time constant of the first tissue is proportional to a thermal conductivity of the first tissue type.

11. The method of claim 10, wherein the thermal time constants are proportional to a thermal conductivity of the first tissue type.

12. The method of claim 11, wherein the thermal conductivity of the second tissue type is twice that of the first tissue type.

13. The method of claim 1, wherein the energy source comprises a radio frequency (RF) energy source.

14. The method of claim 1, wherein controlling the characteristic comprises varying a pulse width of the pulse energy applied during treatment in response to the thermal property of the first tissue type.

15. The method of claim 1, wherein the plurality of electrodes comprise a plurality of bipolar electrodes pairs circumferentially distributed about the radially expandable structure.

16. The method of claim 15, wherein applying the energy comprises energizing selected bipolar electrode pairs, wherein each energized bipolar electrode pair delivers the pulsed energy to a remodeling zone comprising a body lumen tissue between paired electrodes of the respective bipolar electrode pair.

17. The method of claim 16, wherein applying the energy comprises energizing differing bipolar electrode pairs so that the remodeling zones of the bipolar electrodes pairs energized during treatment, in combination, extend about a circumference of the body lumen along the radially expandable structure.

18. The method of claim 17, wherein the bipolar electrode pairs are positioned so the remodeling zones overlap in a circumferential direction.

19. The method of claim 1, wherein the radially expandable structure comprises a balloon, the plurality of electrodes being mounted on a surface of the balloon.

20. A catheter system for heating a body tissue region adjacent a body lumen, the region having both a first tissue type and a second tissue type, the system comprising:

an elongate flexible catheter body having a proximal end and a distal end with an axis therebetween, the catheter body having a radially expandable structure near the distal end;

an energy delivery portion proximate the distal end, wherein the energy delivery portion comprises a plurality of electrodes positioned about the radially expandable structure such that when expanded within the body lumen the plurality of electrodes radially engage the body lumen, wherein the plurality of electrodes engaged against the body lumen complete a plurality of circuits, wherein at least some of the circuits include a first tissue type and a second tissue type while other circuits include a first tissue type without the second tissue type an energy source coupled to the energy delivery portion; and a processor coupled to the energy source, the processor configured to control a pulse characteristic of pulsed energy transmitted from the energy source to each of the plurality of circuits so as to therapeutically treat the second tissue type within the body tissue region by drawing heat from the first tissue type at a rate that avoids significant thermal damage to the first tissue type while building-up heat in the second tissue type, such that the pulsed energy applied to the at least some circuits including the first and second tissue types therapeutically heats the second tissue type while avoiding significant thermal damage to the first tissue and applying the same pulsed energy with the pulse characteristic to the other circuits including the first tissue type without the second tissue type so as to avoid significant thermal damage to the first tissue type.

21. The system of claim 20, wherein the pulsed energy preferentially heats the second tissue type more than the first tissue type, the preferential heating induced at least in part by one or more of the following group of characteristics of the second tissue type: lower thermal conduction than a thermal conduction of the first tissue type, lower specific heat capacity than a specific heat capacity of the first tissue type, less innate blood perfusion than an innate blood perfusion of the first tissue type, and/or larger distance away from well-perfused areas than a distance between well-perfused areas and the first tissue type.

22. The system of claim 21, wherein most of the group of characteristics cause heat to be drawn from the first tissue type at a rate that avoids significant thermal damage to the first tissue type, while allowing heat to build up in the second tissue type.

23. The system of claim 20, wherein the pulsed energy is delivered at an average rate of 0.25 to 5 watts to the body tissue region.

24. The system of claim 20, wherein each pulse of the pulsed energy provides between 04 to 45 Joules to the body tissue region.

25. The system of claim 20, wherein an average rate of pulsed energy delivered to the body tissue region is between about 0.1 and 10.0 times a rate of energy dissipation by the first tissue type.

26. The system of claim 20, wherein a time period between pulses allows the first tissue type to dissipate its heat adequately to avoid thermal damage to the first tissue type by the pulsed energy.

27. The system of claim 26, wherein the energy source comprises a radio frequency (RF) energy source.

28. The system of claim 27, wherein the energy delivery portion comprises a radially expandable structure engaging a plurality of electrode surfaces against the body lumen, wherein the plurality of electrode surfaces against the body lumen complete a plurality of circuits comprising the first tissue type and the second tissue type and pulsed energy is delivered to the plurality of circuits.

29. The system of claim 20, wherein the time period between pulses of pulsed energy is between 0.1 to 180 seconds.

30. The system of claim 20, wherein a thermal time constant for the first tissue type is approximately how long it will take a discrete volume of that given tissue to lose 63% of its heat while undergoing an exponential decay.

31. The system of claim 20, wherein the pulsed energy is delivered to the body tissue region over a duration of at least several differing first tissue type time constants, wherein the thermal time constant of the first tissue is proportional to a thermal conductivity of the first tissue type.

32. The system of claim 31, wherein the thermal conductivity of the second tissue type is twice that of the first tissue type.

33. The system of claim 20, wherein the plurality of electrodes are positioned circumferentially about the radially expandable structure so that the electrodes radially engage the body lumen about a circumference of the body lumen.

34. The system of claim 33, wherein the plurality of electrodes comprise a plurality of bipolar electrode pairs for delivering remodeling energy in a remodeling zone between electrodes of a selected bipolar electrode pair, wherein the remodeling zone includes body lumen tissue between the electrodes of the respective bipolar electrode pair.

35. The system of claim 34, wherein the plurality of bipolar electrodes define a plurality of remodeling zones, which in combination, extend circumferentially about the body lumen.

36. The system of claim 35, wherein the plurality of bipolar electrode pairs are configured so that energizing differing bipolar electrode pairs reduce or eliminate gaps between remodeling zones about the circumference of the body lumen.

37. The system of claim 35, wherein the plurality of bipolar electrodes are positioned so that energizing differing bipolar electrodes pairs delivers energy to the remodeling zones, wherein the remodeling zones overlap about the circumference of the body lumen.

38. The system of claim 35, wherein the radially expandable structure comprises a balloon, the plurality of electrodes being mounted on a surface of the balloon.

39. The system of claim 38, wherein the plurality of electrodes are axially offset along the axis of the catheter body.

40. The system of claim 20, wherein the processor is configured to vary a pulse width of the pulsed energy applied during treatment in response to a thermal property of the first tissue type.

* * * * *